United States Patent [19]

Panandiker et al.

[11] Patent Number: 4,970,067
[45] Date of Patent: Nov. 13, 1990

[54] METHOD AND COMPOSITION TO CONDITION HAIR AND IMPART SEMI-PERMANENT HAIR SET RETENTION PROPERTIES

[75] Inventors: Rajan K. Panandiker, Chicago; Gerald P. Newell, Hanover Park, both of Ill.

[73] Assignee: Helene Curtis, Inc., Chicago, Ill.

[21] Appl. No.: 282,753

[22] Filed: Dec. 12, 1988

[51] Int. Cl.$^5$ .............. A61K 7/075; A61K 7/08; A61K 7/11; A45D 7/04
[52] U.S. Cl. .................... 424/70; 424/71; 252/DIG. 13; 132/203
[58] Field of Search ............ 252/DIG. 13; 424/70, 424/71

[56] References Cited

U.S. PATENT DOCUMENTS 3,842,848 10/1974 Karjala .................. 424/72 X
4,279,996 7/1981 Yoshioka et al. .......... 424/72 X
4,423,032 12/1983 Abe et al. ............... 424/71 X

FOREIGN PATENT DOCUMENTS 2160419 12/1985 United Kingdom ............ 424/71

OTHER PUBLICATIONS

Kerasol, A New Keratin Protein, Gesslein, et al., Cosmetics & Toiletries, vol. 102, Jun. 1987, pp. 56–57.

Primary Examiner—Ellis P. Robinson
Assistant Examiner—Susn S. Rucker
Attorney, Agent, or Firm—Marshall, O'Toole, Gerstein, Murray & Bicknell

[57] ABSTRACT

A method of conditioning the hair and imparting semi-permanent hair set retention properties comprising treating the hair with a composition comprising a protein having a sufficient amount of an amino acid having a disulfide linkage, such as a keratin-based protein that includes the amino acid cystine. The method and composition are essentially pH independent and provide unexpectedly durable, semi-permanent hair set retention properties, and hair conditioning properties, after application to human hair.

38 Claims, 10 Drawing Sheets

4,970,067

METHOD AND COMPOSITION TO CONDITION HAIR AND IMPART SEMI-PERMANENT HAIR SET RETENTION PROPERTIES

FIELD OF THE INVENTION

The present invention relates to a hair treating composition and to a method of setting human hair that conditions the hair and imparts unexpectedly durable, semi-permanent hair set retention properties to human hair. More particularly, the present invention is directed to a hair treating composition comprising from about 0.01% to about 20% by weight of a protein having a sufficient amount of an amino acid having a disulfide linkage, such as a keratin-based protein that includes the amino acid cystine, to provide unexpectedly durable hair set retention properties, and hair conditioning properties, after application to human hair. The composition of the present invention can be applied to the hair from an aqueous or non-aqueous, i.e., alcoholic, solution, spray, emulsion, conditioner, shampoo, bleach, hair color and/or other similar hair treatment and hair fixative products over the pH range of from about 3 to about 12.

BACKGROUND OF THE INVENTION AND PRIOR ART

An individual often desires to change the ordinary straightness of the hair into a curl or wave pattern. This change in the configuration of the hair can be relatively permanent or can be temporary depending upon the process used to treat the hair. To permanently alter the configuration of the hair, the hair is subjected to a process that realigns the configuration of the hair through chemical bond breaking and reformation. Although this process provides a relatively permanent change in hair configuration, the process also tends to damage the hair. To temporarily alter the configuration of the hair, the hair is subjected to a predominantly mechanical realignment of the hair to a new configuration. The new hair configuration is held in place by a non-reacting chemical treatment. This mechanical process is non-damaging to the hair, however, the new configuration of the hair usually is lost as soon as the hair is wetted, such as during shampooing. As a consequence, the hair must be reset almost daily. Therefore, it would be advantageous to provide a hair treating composition for use in a process to alter the configuration of hair that does not damage the hair and yet provides a semi-permanent hair configuration, thereby precluding daily hair setting and hair treating.

In general, the permanent waving of human hair is achieved by chemically breaking the sulfur-to-sulfur, or disulfide, bonds that occur naturally in the cystine component of human hair, and then reforming the disulfide bonds while the hair is wrapped or curled on rods. The sulfur-to-sulfur bonds present in the cystine component of human hair serve to maintain the hair in a naturally straight or naturally curly configuration. Therefore, in order to permanently reshape the hair into a lasting, different configuration, a significant percentage of the sulfur-to-sulfur bonds must be broken and then reformed after the hair is reconfigured into a desired configuration, such as wrapped around a suitable mandrel or roller. In general, the sulfur-to-sulfur bonds of cystine are broken with a composition containing a reducing agent. Then, after the hair is wound into a curl formation around a rod or roller, the disulfide bonds are relinked or reformed while the hair is in the curl configuration by contacting the newly configured hair with an oxidizing agent, such as hydrogen peroxide or a water-soluble bromate.

Different reducing agents, dependent upon the pH of the permanent wave process, are used effectively to break the cystine disulfide bonds that cross-link human hair protein. Generally speaking, the so-called acid permanent wave compositions, having a pH of from 6.5 to 8.5, include reducing agents such as the bisulfites, like ammonium bisulfite, or glycerol monothioglycolate that are capable of breaking the cystine sulfur-to-sulfur bonds at lower pH ranges. The so-called alkaline permanent wave compositions, having a pH in the range of about 7.5 to 9.5, require an alkaline salt of thioglycolic acid, such as ammonium thioglycolate. In the alkaline process, the free alkali of the permanent wave composition penetrates and swells the hair shaft for easier penetration by the reducing agent in order to break the cystine sulfur-to-sulfur bonds. Overall, the alkaline permanent wave compositions produce a stronger, longer lasting curl, whereas the acid permanent wave compositions provide a softer feel but a shorter curl duration.

Human error is one of the primary problems associated with the permanent waving process. In applying the permanent waving lotion, if the beauty operator allows the reducing agent to contact the hair shaft for the incorrect period of time, too many or too few of the disulfide bonds in the hair shaft are broken. The net effect is therefore either seriously damaged hair or hair that has not been treated sufficiently to achieve a permanent wave with long lasting potential. Often the beauty operator has difficulty in determining the correct amount of time that the permanent wave composition should contact the hair because the reducing agent reaction, on the breaking of the disulfide bonds, is dependent upon the amount of heat applied to the hair, the concentration of reducing agent, the pH of the lotion applied, and the condition of hair.

Perhaps the most difficult factor for the beauty operator to assess in determining how long to allow the reducing agent to contact the hair is the condition of the hair at the time of the permanent wave. It is well documented in the literature and the prior art that the hair can be damaged by abuse of hair treating chemicals, such as shampoos, permanent waves, tints, frosts, bleaches, and particularly any hair treatment involving the use of hydrogen peroxide; mechanical hair treatments, such as with thermal appliances; and environmental conditions, like climate and pollution. It is also well known that damaged hair, depending upon the stage and degree of damage to the hair, has significantly different chemical activity to reducing agents than normal or undamaged hair. Therefore, the time of contact between the reducing agent and the hair is important because if too many of the sulfur-to-sulfur bonds in the hair are broken by the reducing agent, the hair will be seriously weakened and may disintegrate.

Ideally, a sufficient number of the sulfur-to-sulfur bonds in the cystine in the hair shafts should be broken in order to give the hair the capability of being reshaped to any desired configuration such as curled around a rod or roller, and the capability of retaining this shape. If too few of the disulfide bonds are broken, the natural configuration of the hair will predominate, causing the hair to retain its previous normal shape because the predominant prior, or natural, bonds in the hair will dictate that the hair remains in its old configuration or shape.

Hydrogen bonds, or the type formed in a hair setting process as opposed to a permanent waving process, are physically broken when wet hair is stretched and wrapped around a roller. When the hair is dried, the hydrogen bonds are reformed in a curled position or shape to set the hair. While the hydrogen bonds act to hold the hair in the new configuration, the covalent disulfide bonds present in cystine are much stronger than the hydrogen bonds and, to a much greater extent than hydrogen bonds, control the ultimate configuration of the hair.

In order to successfully provide a satisfactory permanent wave in the hair, the cystine disulfide bonds, reformed in the hair in the new or curled configuration when the hair is oxidized with the neutralizing agent, should outnumber the cystine disulfide bonds of the old hair configuration. Therefore, when permanent waving, it is desired that a sufficient number of new disulfide bonds, in a new hair configuration, are formed during permanent waving to outweigh the number of old, remaining disulfide bonds that tend to form the hair into its prior or natural configuration, either straight or naturally curled.

Therefore, generally, when permanent waving the hair, the reducing agent lotion is applied to the hair after shampooing the hair, and either before or after the hair is wrapped around suitable rollers. After taking a "test curl" to determine whether the reducing agent has been in contact with the hair for a sufficient time period, the hair is rinsed thoroughly with water while the hair is still on the rollers or rods. Thus, while the hair remains on the rollers or rods in the new, rolled configuration, a neutralizing agent is applied to oxidize and reform the disulfide bonds. The neutralizing agent contains an oxidizing agent, such as hydrogen peroxide or a bromate salt, in order to reform the sulfur-to-sulfur, or disulfide, bonds to leave the hair in a new, relatively permanent configuration that lasts for from about 2 months to about 4 months. The neutralizing agent remains on the hair for approximately 5 to 10 minutes and then is rinsed from the hair. The rods can be removed either before or after rinsing out the neutralizing agent.

However, an individual often does not desire to produce a hair configuration that is relatively permanent, but would prefer to have a more transitory configuration that can be changed readily without having to undergo a second potentially hair-damaging permanent wave process in order to change the relatively permanent hair configuration imparted by the first permanent wave process. In this case, the individual prefers only to set the hair in a particular style for a relatively short time. However, normal hair can be so fine and limp, and so lacking in body, that the hair does not hold a hair set well. Furthermore, the hair can become even less bodied and can be weakened further as a result of being subjected to chemically active hair treatments, such as the permanent waves and tints described above. Additionally, hair can be weakened even further by other contributing factors, such as bleaching by sun exposure and/or chlorinated swimming pool water.

Normal hair is usually hydrophobic. However, many of the chemically active hair treatments remove the natural hydrophobic components from the hair. As a result, as the hydrophobicity of the hair decreases, the relative porosity of the hair increases and the hair tends to absorb water and swell more readily. In such a weakened and porous state, the water-swollen hair is more vulnerable to stretching and breaking.

Since hair setting is basically the process of shaping wet hair by the steps of stretching the hair by curling the hair, fixing the hair in place by drying, then combing to give the finishing touches to provide the desired hairstyle, the overall condition of the hair is an important factor in achieving an acceptable hair set. In particular, the setting of wet hair can be accomplished by making flat curls from strands of hair and fixing the curls with hairpins to produce "pin curls". Similarly, the wet hair can be set by using any of a variety of rollers or curlers to mechanically fix the hair. In either case, the winding of the wet hair is followed by drying, either by ambient air drying, electric drying or hot air drying.

The inherent problem encountered in hair setting is the natural tendency of the hair to return to its natural shape. For example, the set hair returns to its natural shape almost immediately if moistened. Likewise, high humidity conditions accelerate the tendency of the hair to return to its natural shape. Therefore, intensive efforts have been directed to providing a hair set with sufficient holding power to maintain the designed hair style until at least the next shampoo, and therefore giving the hair set a degree of permanency.

As shown by the natural tendency of hair to return to its natural shape, hair is an elastic structure. As a result, the slight deformations in the hair structure resulting from setting the hair are completely reversible. However, the rate of return of the hair to its natural shape is dependent upon the method used to deform, or set, the hair. Hair sets performed with wet strands of hair being rolled tightly, either in curls around the finger or on curlers, followed by drying the hair and in unrolling the curlers after drying, corresponds to the release of the hair from a deformation-causing load. The deformation, or set, obtained can last for several days, but the set will not be retained if the hair is wetted.

The observations of hair deformation and relaxation are related to physical and chemical changes in the protein structure level of hair. Sufficient stretching of the hair causes partial transformation of the α-keratin protein structure of the hair into the β-keratin protein structure of the hair. This structural transformation is accompanied by a shift in relative position of the polypeptide chains that is facilitated by water moistening the hair. The shift in position of the polypeptide chains therefore disrupts the ionic and hydrogen bonds in the hair. During the drying procedure, new ionic and hydrogen bonds are formed that block the return to the α-keratin protein structure of hair. Gradually, the new protein linkages give way under natural forces, such that the hair returns to its original state and length. If the hair is moistened, the return to the α-keratin form is virtually immediate.

Therefore, investigators have sought to delay the combined action of natural forces and moisture that cause the hair to return to its original state by utilizing solutions containing naturally-occurring or synthetic polymers. When applied to the hair from aqueous or aqueous/alcoholic solutions, the polymers leave a film on the hair after drying. The polymeric film promotes cohesion and gives stability to the hair set, and therefore setting lotions containing polymers have been devised to maintain the hold of the hair set. The principal objective of the setting lotion is to cover the styled hair with an invisible polymeric film that will give the styled hair a degree of rigidity and protect the hair style against wind and humidity.

Hair spray products act in a similar manner. The hair spray products are applied to wet hair and generally are not rinsed out. Like hair setting lotions, the hair spray contains polymers, or mixtures of polymers, that remain fixed on the hair and affect the hair in various ways. For example, a "mechanical" effect is exerted on each individual hair. The film-forming polymers are used to provide a flexible sheath of polymeric film on the hair after drying, and therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore resisting the natural forces that return the hair to its natural shape. Finally, the polymeric film protects the hair from humidity. The ability of the polymeric film to attract and absorb water is preferably minimal, such that the polymeric film retards moisture uptake by hair and retards the return of the hair to the α-keratin hair protein structure.

The general principles of hair setting are thoroughly discussed by C. Zviak, in *The Science of Hair Care*, Marcel Dekker, pp. 149–181 (1986). Zviak reviews both the polymers used in hair setting products and the formulation principles used to produce a hair set product that provides such beneficial hair set properties as improved hair style hold, easy application and combing, quick drying and non-stickiness, good hair body and bounce, increased hair volume and gloss, and hydrophobicity. It is evident that in the formulation of any end-use product, some of these benefits must be sacrificed to some degree to achieve a competing benefit. Therefore, the formulation of hair set products has proved difficult, and, as a result, hair set products have been developed in a variety of product forms.

The prior art reveals that nonionic, cationic and anionic polymers have been used in hair set products, with the anionic polymers providing the best hair set results. However, anionic polymers also have disadvantages, such as high water solubility, therefore low hydrophobicity, and low substantivity to hair fibers, therefore easy elimination from the hair by combing and brushing. As a result, investigators have continued to search for compounds and compositions that provide the benefits of an anionic surfactant-based hair set product plus an improved durability of the hair set. As previously mentioned, to overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners and shampoos.

Although commercially available products relying upon polymeric materials produce bodying effects on the hair, these products usually do not provide improvements in hair hydrophobicity against the known adverse effects of humidity in maintaining a hair style. In some cases, the hair treating products make the hair hard to comb or can absorb moisture themselves. One other effort to make hair hydrophobic is to apply oily hair dressings and creams to the hair, wherein the oily product is left on the hair to act as a physical barrier against moisture uptake. However, these oily products provide only a temporary barrier that is removed when the consumer washes her or his hair. In addition, these oily products frequently impart the hair with a dull coating, thereby sacrificing the bodying benefits desired by persons having fine, limp, porous hair. Consequently, in using presently available commercial products, consumers must sacrifice certain desirable physical characteristics of the hair in order to achieve or improve other desirable physical characteristics.

The present invention relates to a composition and method of treating the hair to condition the hair and to improve the physical properties of the treated hair. It has been found that by treating the hair with a composition comprising a protein having a sufficient amount of an amino acid having a disulfide linkage, such as a keratin-based protein that includes the amino acid cystine, the hair is conditioned and the physical properties of the hair are improved such that the hair will retain the shape of the hair set and will not revert to its natural shape upon contact with moisture. Furthermore, surprisingly and unexpectedly, hair treated with the composition of the present invention still will retain the shape of the hair set after several subsequent shampooings. Thus, the improved hair set retention properties imparted to the hair upon treatment with the composition of the present invention obviates the need to treat the hair each day or after each shampooing. In addition, the method and composition of the present invention provides a semi-permanent hair set that avoids the hair-damaging, reduction/oxidation permanent wave processes.

Proteins have been used in the hair care industry for a number of years. Presently, several commercial end-use hair-care products include proteins in order to provide some functional or esthetic benefit to the hair care product. The proteins used in hair care products differ in their physical properties, appearance and functional properties depending upon the source of the protein and the method used to hydrolyze the protein. For example, silk polypeptides, silk amino acids, hydrolyzed animal keratin, collagen and soya proteins each exhibit different physical and chemical properties and each has been used in hair care products to exploit the particular advantages of that protein. Furthermore, derivatized proteins, such as steardimonium hydrolyzed animal protein and triethanolamine lauroyl animal keratin amino acids are available specifically for use in cationic and anionic systems, respectively, because these derivatized proteins are considered to have a higher affinity for hair than the native underivatized protein. Generally, proteins and protein derivatives are used as conditioning agents to improve one or more of the following hair properties: combability, sheen, manageability, texture, body, and strength/elasticity.

Usually, the interaction between the hair and a protein is purely ionic in nature as a result of hydrogen bonding and some van der Waal interactions. Consequently, the bonds between the hair and the protein are easily broken by the moisture in air or water. Therefore, as in the usual synthetic polymer-based hair setting composition, the protein-based hair setting composition shows poor wash-fastness and is easily removed by wetting or shampooing the hair. As a result, the conditioning effects and hair set retention properties imparted to the hair by most protein-based hair setting compositions is only temporary.

However, a covalent bond between a protein and the hair can be formed if the protein includes an amino acid having a sulfur-to-sulfur, or disulfide, linkage, like the disulfide linkage present in the amino acid cystine. Normally, such proteins are applied to the hair in a redox system, like the redox systems used in a permanent wave process as described above, in order to provide a hair set and hair conditioning properties to the hair. An example of a protein applied to the hair in a permanent wave process is the protein sold under the brandname KERASOL, available from Croda Inc., N.Y., N.Y. KERASOL is a relatively high molecular weight keratin-based protein prepared by the cold hydrolysis of cattle hooves, and contains about 0.6% by weight of the amino acid cystine. Typically, KERASOL is applied to the hair as a post-reduction step in the permanent waving process. As will be described more fully hereinafter, a significant improvement in the condition of the hair is perceived if the KERASOL protein is applied to the hair either immediately after application of the reducing thioglycolate lotion or after subsequent rinsing of the reducing lotion from the hair. Furthermore, it has been disclosed that a cystine-containing protein can be added directly to the reducing thioglycolate solution to produce cystine residues in the thioglycolate solution that can be applied, thus subsequently covalently bonded, to the hair to impart superior conditioning properties.

A protein including a sufficient amount of an amino acid having a disulfide linkage is known to covalently bond to the hair when the protein is applied during a permanent wave process. The prior art teaches that proteins including an amino acid having a disulfide linkage are substantive to the hair, but that these proteins will not covalently bond to the hair when applied from non-reactive vehicles, such as shampoos and conditioners. To achieve covalent bonding between the cystine-containing protein and the hair, the prior art teaches that it is necessary to break the cystine disulfide bonds present in the hair keratin by a permanent wave process, to apply the cystine-containing protein at an appropriate step in the permanent wave process, and then to reform the cystine disulfide bonds, both within the hair and between the hair and the cystine-containing protein during the neutralization step of the permanent wave process. The prior art consistently emphasizes that if the cystine-containing protein is not applied at the appropriate stage of the permanent waving process, that the cystine-containing protein can not covalently bond to the hair through disulfide linkages.

For example, J. Chester and G. Mawby, in the publication "Permanent Hair Conditioning", *Manufacturing Chemist*, April 1987, pp. 53 and 55, teach that a permanent hair-conditioning effect can be achieved by covalently bonding a suitable conditioning agent to the hair keratin. The authors used a hydrolyzed keratin-based protein, containing both the amino acid cystine and cystine residues, as the conditioner, and covalently bonded the sulfur atoms present in the cystine residues of the keratin-based protein to the sulfur atoms present in the cystine residues of the hair by a reduction/oxidation treatment, such as a permanent waving process. As will be described more fully hereinafter, the authors found that a permanent conditioning effect is achieved when the cystine-containing protein was applied to the hair at any of the steps in a permanent waving process before the application of the oxidizing lotion. The authors likewise found that no permanent conditioning effect was achieved if the cystine-containing protein was applied after the application of the oxidizing lotion. Therefore, the cystine-containing protein had to be applied to the hair when the hair was in its reduced state, such that the sulfide moieties of the reduced hair could react with the disulfide bonds, or the reduced sulfide moieties, of the cystine-containing protein to form a covalent bond. The authors teach that the formation of a covalent bond between the hair and the cystine-containing protein is not possible after the oxidizing lotion is applied to the hair because the oxidizing lotion converts the reactive sulfide moieties of the reduced hair and of the keratin-based protein back to the relatively unreactive disulfide linkages of the natural hair and of the protein. The authors further found that maximum amount of covalent bonding of the hair to the cystine-containing protein occurred when the cystine-containing protein was applied to the hair just prior to application of the oxidizing lotion of the permanent waving process, and that no covalent bonding occurred when the cystine-containing protein was applied after the application of the oxidizing lotion of permanent waving process.

A. K. Puri and R. T. Jones, in "An Approach To Permanent Hair Conditioning", Preprints of the XIVth I.F.S.C.C. Congress, Barcelona, Vol. II, pp. 1153–1176 (1986), also showed the necessity of having first to reduce the hair, such as with a thioglycolate solution, before applying a protein that includes an amino acid having disulfide linkages to the hair, in order to form a covalent bond between the hair keratin and the protein. The authors similarly reported that covalent bonds between the hair and the protein did not form if the protein was applied to the hair after application of the oxidizing solution of the permanent waving process.

Karjala, in U.S. Pat. No. 3,842,848, teaches that improved conditioning properties are imparted to the hair by adding a cystine-containing protein directly to a thioglycolate solution in order to covalently bond the disulfide-containing protein to the hair. The method of Karjala, wherein the hair is treated with a reducing solution, that further includes a cystine-containing protein in order to break the disulfide bonds present in the hair keratin, is very similar to the normal permanent wave process. Then, a subsequent treatment with an oxidizing agent reforms the disulfide bonds that occur naturally in the hair, and further forms disulfide bonds between the hair and the cystine-containing protein that was added to the reducing solution in order to impart permanent conditioning properties to the hair.

A related method is disclosed in U.K. Patent Application GB 2,114,616, wherein a semi-permanent hair conditioning effect is achieved by precipitating a complex formed through the interaction between a cationic polymer that is present in the reducing solution and an anionic detergent that is present in the neutralizer solution onto the hair fibers. This method differs from the method of the present invention in that a covalent bond does not form between the protein-based conditioning agent and hair fibers to impart a more permanent hair conditioning effect. U.K. Patent Application GB 2,160,194 likewise teaches improving the condition of hair, skin or nails by a process of reducing the hair, rinsing the hair, applying an aqueous solution of a cystine-containing protein hydrolyzate to the hair, then applying a neutralizing solution to the hair. This process, however, damages the hair as a result of the reduction-oxidation steps required to covalently bond the cystine-containing protein to the hair. S. Naito, et al. in "Sorption Of Keratin Hydrolyzate To Hair And The Cosmetic Effect", Preprints of the XIVth I.F.S.C.C.

Congress, Barcelona, Vol. II, pp. 1178–1193 (1986), demonstrates that the keratin-based hydrolyzates are in fact covalently bound to the hair if the hair first is reduced, then oxidized.

In contrast to the relatively permanent hair set retention properties afforded by permanent wave processes, to date, the compositions and methods used only to set hair have suffered from poor set retention times, from sacrificing one beneficial hair property in order to achieve another beneficial hair property, and/or from abnormally long times to treat the hair. Similarly, the compositions and methods used to permanently wave the hair have suffered from the disadvantages of serious hair damage due to the reduction-oxidation process coupled with operator error, such as too strong of reduction solution or too long of a contact time. Accordingly, prior to the present invention, no known method or composition has been employed to effectively condition hair within a few minutes and, simultaneously, to provide a semi-permanent hair set that is preserved through several shampooings subsequent to the hair conditioning and setting treatment.

Therefore, in accordance with the present invention, hair conditioning and hair set retention properties are surprisingly and unexpectedly improved by a method of contacting the hair with a composition comprising a protein having a sufficient amount of an amino acid having a disulfide linkage, such as a keratin-based protein that includes the amino acid cystine. The compositions of the present invention can be applied to the hair from an aqueous or a non-aqueous, such as alcoholic, vehicle at ambient temperature and are allowed to contact the hair for relatively short times to provide the benefits and advantages of a semi-permanent hair set without damaging the hair as a result of harsh reduction and oxidation reactions. Therefore, as will be demonstrated more fully hereinafter, the method and composition of the present invention both condition the hair and impart an esthetically-pleasing, semi-permanent hair set without damaging the hair and that is durable through several subsequent shampooings.

SUMMARY OF THE INVENTION

In brief, the present invention relates to a composition and method of treating human hair. More particularly, the present invention relates to a method of treating the hair, whereby contacting the hair with a composition comprising a protein having a sufficient amount of an amino acid having a disulfide linkage, such as a keratin-based protein that includes the amino acid cystine, conditions the hair and simultaneously imparts semi-permanent hair set retention properties to the hair. The easy-to-apply composition provides a strong, semi-permanent hair set, without damaging the hair, and leaves the hair unexpectedly soft. Surprisingly and unexpectedly, human hair treated with the composition of the present invention demonstrates improved physical characteristics, such as gloss, thickness, combability, softness and body, and also exhibits exceptional hair set retention properties, such that the hair can be rewet or shampooed several times after application of the hair treating composition without having to reapply a hair treating composition before styling the hair. Furthermore, the composition and method of the present invention impart conditioning and semi-permanent waving characteristics to the hair without damaging the hair by a harsh chemical reduction-oxidation process.

Therefore, it is an object of the present invention to provide a hair treating composition that conditions the hair and simultaneously imparts semi-permanent hair set retention properties to the hair without damaging the hair.

It is also an object of the present invention to provide a hair treating composition comprising a protein having a sufficient amount of an amino acid having a disulfide linkage.

Another object of the present invention is to provide a hair treating composition that is capable of conditioning the hair and simultaneously imparting semi-permanent hair retention properties to the hair over a pH range of about 3 to about 12.

Another object of the present invention is to provide a method of treating human hair with a hair treating composition to achieve improved hair set retention properties and, simultaneously, to condition the hair.

Another object of the present invention is to provide a method of treating human hair by contacting the hair with a composition having a pH of between about 3 and about 12 and comprising a protein having a sufficient amount of an amino acid having a disulfide linkage, then drying the hair, to condition the hair and to achieve a semi-permanent hair set having sufficient durability to withstand several subsequent shampooings.

Another object of the present invention is to provide a method of treating human hair to yield semi-permanent hair sets by treating the hair with a composition comprising from about 0.01% to about 20% by weight of a protein comprising a sufficient amount of an amino acid that contains a disulfide linkage, such as cystine.

Another object of the present invention is to provide a method of treating human hair to yield semi-permanent hair sets by treating the hair with a composition comprising from about 0.01% to about 20% by weight of a keratin-based protein.

Another object of the present invention is to provide a composition to condition the hair and, simultaneously, to impart semi-permanent hair set retention properties to the hair by cleaving a sufficient number of sulfur-to-sulfur, or disulfide, bonds in human hair, without the use of a reducing solution, such that the hair can be reconfigured in a different configuration. The cleaved disulfide bonds in the human hair are reformed with the disulfide linkages, or the cleaved disulfide linkages, present in a protein having an amino acid containing a disulfide linkage, to simultaneously condition the hair and maintain the new hair configuration for an extended time period.

Another object of the present invention is to provide a new and improved semi-permanent hair setting composition capable of breaking sulfur-to-sulfur bonds in the hair, but not containing a harsh reducing agent, and therefore causing no damage to normal hair, or no further damage to tinted, frosted, bleached or other substantially damaged hair.

Still another object of the present invention is to provide a method of treating the hair to yield semi-permanent hair sets by contacting the hair with an aqueous or non-aqueous, i.e., alcoholic, spray, solution, emulsion and/or shampoo to treat the hair, without heat, in either a rinse-off or leave-on method.

BRIEF DESCRIPTION OF THE DRAWINGS

The above and other objects and advantages and novel features of the present invention will become apparent from the following detailed description of the preferred embodiments of the invention illustrated in the accompanying figures illustrating the enhanced hair set retention properties and the hair conditioning properties achieved by using the method and composition of the present invention, wherein.

DETAILED DESCRIPTION OF THE PREFERRED EMBODIMENT

The hair treatment composition of the present invention comprises a protein having a sufficient amount of an amino acid having a disulfide linkage; and has a pH of from about 3 to about 12.

A protein including a sufficient amount of an amino acid having a disulfide linkage generally contains the naturally-occurring amino acid, cystine. As a result, the protein utilized in the method and composition of the present invention is generally a keratin-based protein. Keratin is a protein obtained from hair, wool, horn, nails, claws, beaks, scales, nerve tissue and the membranes of egg shells. Keratin contains all of the common, naturally-occurring amino acids, but differs from other fibrous structural proteins, such as the protein collagen that makes up the connective tissue in mammals, because keratin has a high cystine content. Cystine is important in the hair care industry because it is the only naturally-occurring amino acid that has a sulfur-to-sulfur, or disulfide, chemical linkage. Therefore, the protein utilized in the present invention is usually, but not necessarily, a keratin-based protein; however, any protein containing a sufficient amount of an amino acid having a disulfide linkage, like cystine, can be used in the method and invention of the present invention.

Keratin itself has such a high molecular weight that it cannot be used in the method and composition of the present invention. However, keratin can be hydrolyzed, either by acid or alkali, to yield lower molecular weight keratin fragments, or keratin hydrolyzates, that are soluble in water. It is these keratin hydrolyzates that can be formulated into aqueous or non-aqueous, such as alcoholic, end-use hair treatment products for use in the method of the present invention. It has been found that keratin hydrolyzates having an average molecular weight of from about 20,000 to about 1,000,000 possess sufficient water or non-aqueous solvent solubility to permit the manufacture of a useful and stable hair treatment product. Furthermore, it has been found that keratin hydrolyzates having an average molecular weight of from about 50,000 to about 300,000 provide the full benefits and advantages of the present invention. A particularly useful keratin hydrolyzate, having an average molecular weight of approximately 125,000, is commercially available from Croda, Inc., N.Y., N.Y. under the trade name KERASOL. KERASOL is a keratin hydrolyzate obtained from the cold hydrolysis of cattle hooves, and is up to 15% by weight soluble in water.

In contrast to the teachings of the prior art, it has been discovered that such keratin hydrolyzates, or a similar protein hydrolyzate having a sufficient amount of an amino acid, like cystine, with a disulfide linkage, can bond to hair both to condition the hair and to impart semi-permanent hair set retention properties without having to subject the hair to a harmful chemical reduction-oxidation process.

Figure 1:
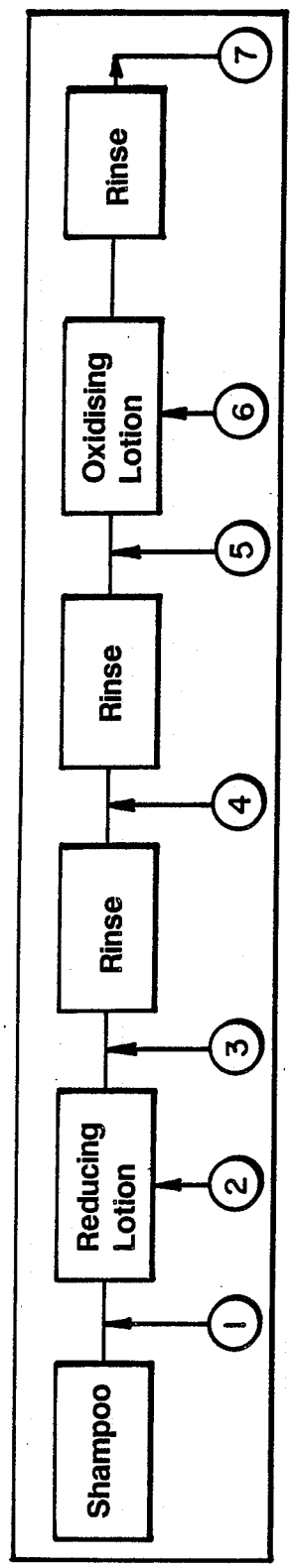
FIG. 1 is a schematic diagram showing a typical permanent wave process. The numerals 1 through 7 demonstrate steps in the permanent wave process that a hair conditioner and/or a hair set treatment can be applied to the hair.

As previously discussed, the prior art teaches that keratin hydrolyzates, containing a sufficient amount of the amino acid cystine, can be covalently bound to hair when the keratin hydrolyzate is applied to the hair at the proper step of a permanent waving process. Referring to the schematic diagram FIG. 1, the appropriate steps to add the keratin-based hydrolyzate is any of steps 1 through 5, wherein the hair, and/or the keratin-based hydrolyzate, is in the reduced state. Therefore, the cystine residues of the hair are available to react with the cystine residues of the keratin hydrolyzate during the oxidation step. In accordance with the teachings of the prior art, if applied at the inappropriate time, such as concurrently with or after application of the oxiding solution, i.e., step 6 or step 7 of the permanent waving process depicted in FIG. 1, the keratin hydrolyzate would not react with the hair to form a covalent sulfur-to-sulfur hair-to-keratin hydrolyzate bond. However, surprisingly and unexpectedly, and in accordance with the method and composition of the present invention, it has been found that it is not necessary to reduce the hair before a reaction between the hair and the keratin hydrolyzate occurs to form a bond. It has been found that, when included in an aqueous and/or a non-aqueous vehicle, a keratin hydrolyzate can bond to the hair, without a pre-reduction and a post-oxidation step, to impart a semi-permanent hair set and to condition the hair.

To achieve the full advantage of the present invention, the combination of amino acids comprising the protein hydrolyzate should include at least 0.1%, on a weight of amino acid to weight of protein hydrolyzate basis, of an amino acid containing a disulfide linkage, such as cystine. Preferably, the protein hydrolyzate is comprised of a combination of amino acids such that the amino acid containing a disulfide linkage is greater than 0.1% by weight of the protein hydrolyzate. It has been found that the proteins comprising about 0.1% or greater by weight of an amino acid, like cystine, have a sufficient number of disulfide linkages in the protein hydrolyzate available to bond with the disulfide linkages of the hair. As will be discussed more fully hereinafter, more improved hair set retention properties are achieved as the percentage of disulfide-containing amino acids, like cystine, in the protein hydrolyzate increases.

The percentage amount of the disulfide-containing protein hydrolyzate present in the hair treating composition is limited only by the solubility of the protein hydrolyzate in the aqueous and/or non-aqueous carrier vehicle of choice, or by the ability to emulsify the protein hydrolyzate to form a stable aqueous emulsion. Protein hydrolyzates of lower molecular weight, such as below about 20,000, have excellent solubility in both aqueous and/or non-aqueous carriers. However, protein hydrolyzates of molecular weight lower than about 20,000 do not condition the hair sufficiently and do not improve hair set, or curl set, retention properties sufficiently. Conversely, the higher molecular weight protein hydrolyzates, such as protein hydrolyzates of molecular weight greater than about 1,000,000, do provide sufficient hair conditioning and hair set retention properties, but these high molecular weight protein hydrolyzates are not sufficiently soluble in aqueous and/or non-aqueous carriers to be practically useful. Therefore, it has been found that the protein hydrolyzates having a molecular weight in the range of from about 20,000 to about 1,000,000, and preferably in the range of about 50,000 to about 300,000, are sufficiently soluble in aqueous and/or non-aqueous carriers, possess sufficient hair conditioning properties, and impart semi-permanent hair set retention properties to provide the unexpected advantages and benefits of the present invention. Therefore, in accordance with the method of the present invention, it has been found that an aqueous or non-aqueous hair treating composition comprising from about 0.01% to about 20%, and preferably from about 0.25% to about 3%, by weight of a disulfide-containing protein hydrolyzate, based on the total weight of the hair treating composition, simultaneously conditions the hair and imparts semi-permanent hair set retention properties that persist through several subsequent shampooings.

Therefore, the percentage amount of the disulfide-containing protein hydrolyzate in the hair treating composition is limited essentially by the solubility of the protein hydrolyzate in the aqueous or non-aqueous carrier vehicle of choice. However, other considerations, such as product esthetics and the type of commercial end-use product desired, like a hair shampoo, hair conditioner, or hair set lotion, also determines the amount of protein hydrolyzate present in the composition of the present invention. As will be discussed more fully hereinafter, it has been found that hair treating compositions including a greater percentage of disulfide-containing protein hydrolyzate provide more cystine disulfide moieties for potential contact and interaction with disulfide moieties in the hair, and therefore provides better hair conditioning and better hair set retention properties.

It also has been demonstrated that regardless of the percentage amount of the disulfide-containing protein hydrolyzate present in the hair treating composition, the full advantages of the present invention are realized for hair treating compositions of the present invention over the broad pH range of about 3 to about 12. The utility of the method and composition of the present invention over such a broad pH range therefore permits the incorporation of a wide variety of cosmetically beneficial components and additives into the hair treating composition without detracting from the basic function of the composition in regard to conditioning the hair and in regard to imparting semi-permanent hair set retention properties.

Therefore, other common cosmetic components and additives that can be incorporated with the essential ingredients of the present invention, as long as the basic properties of the hair setting composition are not adversely affected, include, but are not limited to, commonly used fragrances, dyes, hair colorants, opacifiers, pearlescing agents, dandruff control agents, hydrotropes, foam stabilizers, solubilizers, preservatives, water softening agents, acids, bases, buffers and the like. These optional components and additives usually will be present in weight percentages of less than about 2% each, and from about 5% to about 10% in total.

The hair setting composition vehicle is generally predominantly water, but organic solvents also can be used alone or included in an aqueous composition in order to solubilize compounds that are not sufficently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether; and mixtures thereof. These non-aqueous solvents can be present in the hair setting composition of the present invention in an amount from about 1 to about 100% by weight and in particular from about 5 to about 50% by weight, relative to the total weight of the carrier vehicle in the composition.

As will be discussed more fully hereinafter, the hair setting compositions of the present invention preferably are thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount from about 0.1% to about 3%, and preferably from about 0.25% to about 1%, by weight relative to the total weight of the composition.

The hair setting compositions also can include anionic, amphoteric or nonionic surfactants to impart cleansing and/or emulsifying properties to the composition. Likewise, the compositions can contain other emulsifiers, fatty alcohols, humectants and similar materials to provide conditioning properties, esthetic properties and desirable physical properties to the composition. Generally, such optional ingredients are present in weight percentages of from about 0.1% to about 10% each, and from about 0.1% to about 20% in total, relative to the total weight of the composition.

For example, representative nonionic surfactants that can be included in the hair setting composition of the present invention include esters of polyols and sugars; the polyethoxylated and/or polypropoxylated alkylphenols; the polyhydroxylated polyethers of fatty alcohols; and the condensation products of ethylene oxide with long chain amides. Similarly, representative anionic surfactants include alkali metal salts, ammonium salts or salts of amines or amino alcohols of fatty acids, such as oleic acid; of the sulfates of fatty alcohols, principally $C_{12}$–$C_{14}$ and $C_{16}$ fatty alcohols; of the sulfates of polyethoxylated fatty alcohols; of the alkylbenzenesulfonates, such as those wherein the alkyl moiety has 12 carbon atoms; or of the alkylarylpolyether sulfates and monoglyceride sulfates. All these nonionic and anionic surfactants, as well as numerous others not cited here, are well known in the art and are fully described in the literature.

In accordance with the method of present invention, several hair setting compositions were prepared, then applied to human hair, to demonstrate the semi-permanent hair set retention and improved hair conditioning properties afforded by compositions having a pH of from about 3 to about 12 and comprising a protein having a sufficient amount of an amino acid having a disulfide linkage, such as a keratin-based protein that includes the amino acid cystine. Representative hair setting compositions are presented in Example I, showing the range of unthickened compositions of the present invention. The compositions of Example I were prepared by adding the ingredients in the order listed with thorough mixing to yield a water-thin solution of pH 8.0 to 8.5.

Example I

| Unthickened Hair Setting/Conditioning Compositions | |
|---|---|
| Ingredient | Wt % |
| Soft Water (vehicle) | q.s. to 100% |
| Cystine-containing protein (KERASOL, available from Croda, Inc., N.Y., N.Y.; 15% by weight aqueous solution of keratin hydrolyzate; MW of approximately 125,000) | 0.06%–27% |
| Preservative | q.s. |
| Sodium Hydroxide or Citric Acid solution (pH adjustment) | q.s. to pH 8.0–8.5 |
| Dye, fragrance and other optional ingredients | as desired |

To demonstrate the new and unexpected results achieved by the method and composition of the present invention, several hair setting compositions were prepared in accordance with the formulation illustrated in Example I, then applied to freshly-shampooed human hair. As will be discussed in more detail hereinafter, it was demonstrated that applying a composition comprising a cystine-containing protein, such as KERASOL, to hair, when the hair is in its natural unreduced state, provides a substantial improvement in hair conditioning properties and imparts semi-permanent hair set retention properties.

The treated hair was tested to determine the ability of the hair treatment composition of the present invention to maintain the treated hair in a particular hair set. In particular, the various hair treating compositions were tested by applying one gram of the hair treating composition to clean freshly-shampooed and towel dried, white tresses of normal virgin human hair, available commercially from DeMeo Brothers, New York, N.Y. The six inch hair tresses, each weighing two grams, were attached to a plastic tab at the root end. In each test, the composition was applied and combed through the hair. Then the treated hair tresses were rolled on styling rollers and dried overnight. After drying, the rolled tresses were placed in a chamber, maintained at a constant 26.6° C. and 80% relative humidity, for equilibration.

The rollers then were removed from the hair tresses and the tresses were suspended freely in front of a panel graduated in inches. The initial length of the hair tress was recorded, and as the tresses relaxed in the 26.6° C. and 80% relative humidity chamber, tress length measurements were taken after one hour and after 24 hours. The percent set retention, or percent curl retention, after one hour and after 24 hours for hair treated with a composition of Example I containing either 0%, 1.0%, 1.5%, 2.0% or 3.0% of the cystine-containing protein KERASOL was calculated and plotted in FIG. 2 from the tress length measured at the desired time according to the procedure fully described below. This procedure was replicated by applying each hair treatment composition to three different tresses of hair, and the average value of the three replicate tests was used in the calculations.

The procedure to determine the percent set retention values is fully described in the publication "Set Relaxation of Human Hair", P. Diaz and M. Wong, *J.Soc. Cosmet.Chem.*, 34, 205–212 (1983). This publication describes a method of quantifying hair set retention properties for hair treated and set in the method described above. The publication shows that the amount of set retained by the hair after a particular time interval, or the percent set, or curl, retention of a hair tress, can be calculated for a time (t) after a roller has been removed from a tress of set hair from the following formula:

$$\% \text{ Set Retention} = \frac{L - L_t}{L - L_0} \times 100\%, \qquad \text{(Eq. 1)}$$

wherein
L = length of the fully extended hair tress,
$L_0$ = length of the hair curl at the onset of relaxation (t=0),
$L_t$ = length of the hair curl at time t
t = time elapsed since roller was removed from the set hair curl.

This measurement method has proven to be very precise and reliable, thereby making it possible to evaluate both the hair set retention properties of commonly used hair set compositions and the effectiveness of various components included in the hair set compositions. In addition, tresses of hair set only with water also are included in the test as a control.

Diaz and Wong found that the tresses lengthen under the effect of the 80% relative humidity as a function of time. The lengthening process therefore provides important and relevant information concerning the effectiveness of hair setting compositions. By measuring the length of the hair curl of a treated or untreated hair tress at intervals over time, the percent set retention of the tress at a particular time can be calculated, and the percent set retention of the tress over time can be graphed.

Figure 2:
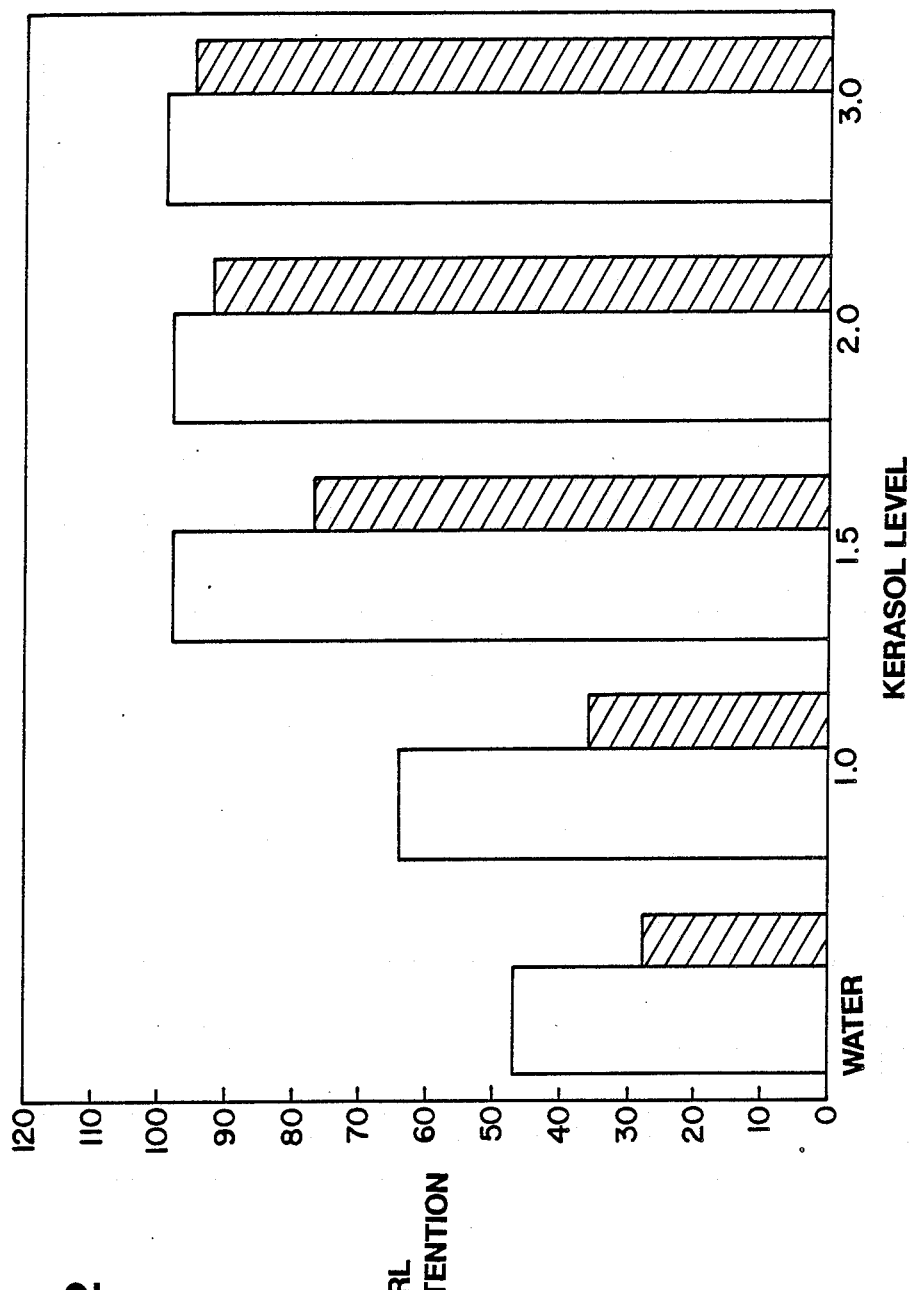
FIG. 2 is a graph of % curl retention after one hour and after 24 hours vs. percentage amount of cystine-containing protein present in the composition used to treat the hair.

FIG. 2 is a graph of % curl retention, calculated according to Eq. 1, for hair tresses treated with compositions containing 0%, 0.15%, 0.23%, 0.30% and 0.45% by weight of a cystine-containing keratin hydrolyzate protein (corresponding to 0%, 1%, 1.5%, 2%; and 3% of KERASOL included in the hair treating composition) one hour after onset of curl relaxation and 24 hours after onset of curl relaxation. For the control test, using only water (0% keratin hydrolyzate), it was observed that the % set retention after 1 hour is less than 50% and after 24 hours is less than 30%. The percent hair set retention values demonstrate the effect of 80% relative humidity upon a hair set when the hair is untreated. However, it also was observed that applying a composition containing 0.15% by weight keratin hydrolyzate to the hair increases the % set retention after 1 hour to approximately 65%, and after 24 hours to greater than 35%. Furthermore, increasing the amount of keratin hydrolyzate in the hair setting composition to 0.23%, 0.30% or 0.45% leads to a 1 hour percent curl retention of 100%, and a 24 hour percent curl retention of about 78%, about 93% and about 96%, respectively. These percent curl retention results show that by applying a composition containing 0.15% of a keratin hydrolyzate to the hair improved hair set retention properties result; and that by applying a composition containing 0.23% of a keratin hydrolyzate to the hair, essentially total curl retention is achieved over the short term. Furthermore, by increasing the amount of keratin hydrolyzate, such as up to approximately 0.30% by weight of the composition, greater than 90% curl retention is achieved over the long term. Treating human hair with compositions including greater percentages of the keratin hydrolyzate gave correspondingly improved hair set retention properties.

Furthermore, in conducting the tests graphed in FIG. 2, in addition to finding that increasing the amount of keratin hydrolyzate in the composition leads to increased curl retention, a distinct thiol odor was detected after the application of a hair setting composition of Example I to the hair. The detection of a thiol odor indicates that a chemical reaction occurred between the keratin hydrolyzate and the hair because neither the hair nor the hair-treating composition possessed a distinct thiol odor before contact of the hair-treating composition with the hair. Such a result is totally unexpected in light of the teachings of the prior art, wherein it is disclosed that the hair must be in a reduced state, followed by a neutralizing oxidation step, before a reaction can occur between the hair and keratin hydrolyzate. Under the normal reduction-oxidation conditions of a typical permanent wave process, an identical thiol odor is detected as that detected when using the composition and method of the present invention, therefore demonstrating that a chemical reaction is occurring during the method of the present invention between the hair and the hair treating composition.

In addition, hair treated with a composition of the present invention comprising a sufficient amount of the cystine-containing protein hydrolyzate maintained the desired hair set through several subsequent shampooings. This surprising and unexpected result further showed that the keratin hydrolyzate is bound to hair without having to employ the hair-damaging reduction and oxidation steps. Accordingly, the keratin hydrolyzate is not rinsed from the hair like present day hair setting compositions, that contain such hair setting components as polymers, at the first shampooing. In contrast, the keratin hydrolyzate remains on the hair to maintain the hair set in the desired hair set configuration through several shampooings, and consequently the hair set configuration can last for several days. As a result, an individual desiring a new and semi-permanent hair configuration does not have to undergo a permanent wave process that damages the hair, and in addition does not have to reapply a non-damaging, but easily removable, hair setting composition to the hair each day. Therefore, the method and composition of the present invention provides a semi-permanent hair set that affords both the benefits of a present day hair setting composition and of the benefits of a hair-damaging permanent wave without damaging the hair.

To demonstrate that hair treated with the hair treating compositions of the present invention provide semi-permanent hair set retention properties, hair treated with a composition containing 0%, 0.15%, 0.23%, 0.30% and 0.45% by weight of a keratin hydrolyzate was shampooed two times using a common, commercial sodium lauryl sulfate-based hair shampoo (SALON SELECTIVE #5 SHAMPOO, available from Helene Curtis Inc., Chicago Il.) by working the shampoo into a lather for 1 minute, then rinsing the shampoo from the treated hair for 30 seconds with water. After the second shampooing, the hair was blow-dried and the body of the hair was evaluated by a panel of experts.

Figure 3:
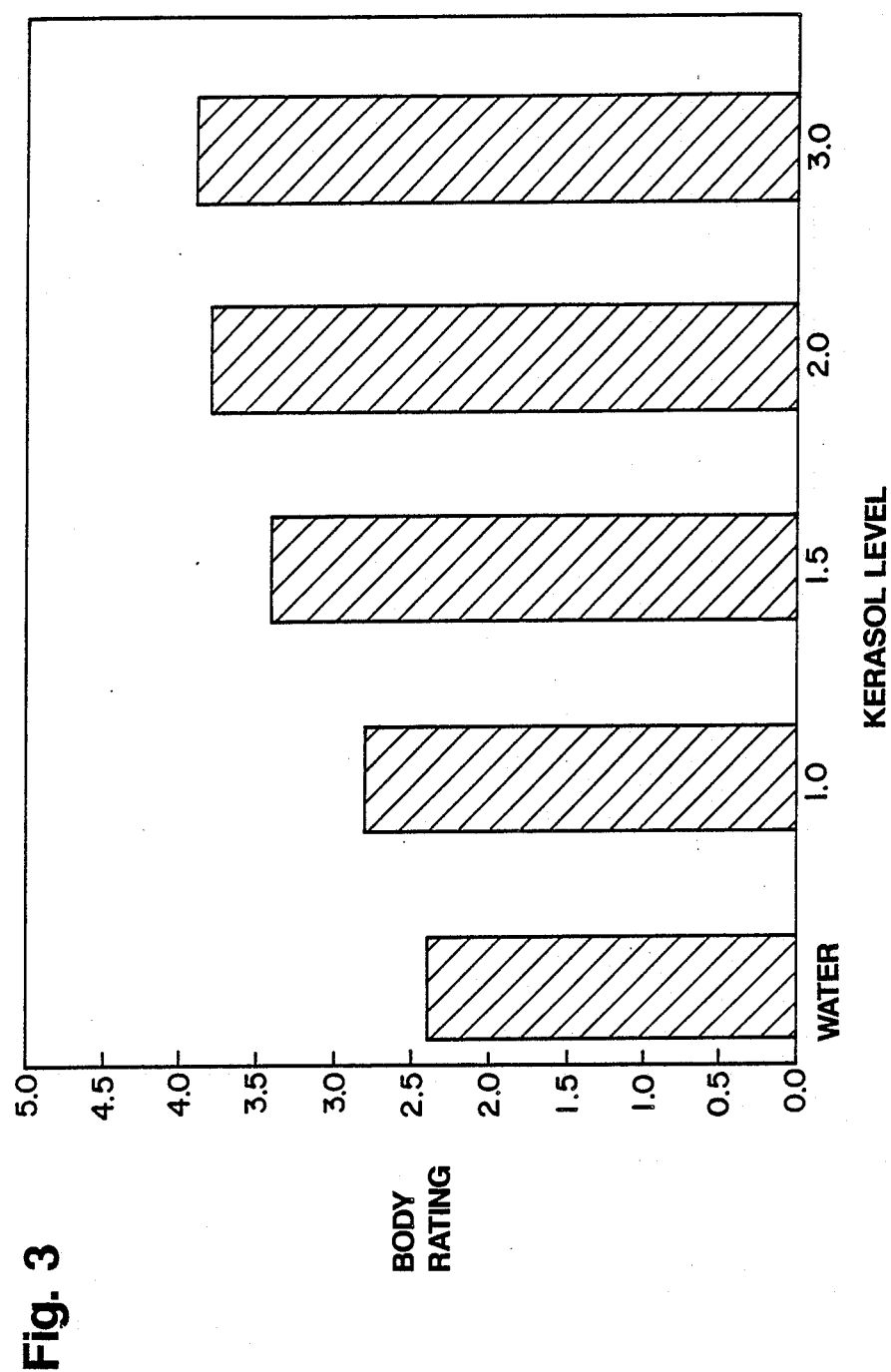
FIG. 3 is a graph of subjective body rating, showing the relative condition of the hair after two shampooings vs. percentage amount of cystine-containing protein present in the composition used to treat the hair.

As demonstrated in FIG. 3, the experts rate the hair on a subjective scale of 0 to 5. The average body rating of five experts was graphed in FIG. 3, with the control hair swatch, treated only with water, showing a body rating of slightly less than 2.5. In general, the body rating of hair is the bulk or fullness of the hair. Usually such properties as hair fiber diameter, hair fiber density, stiffness, configuration, friction between hair fibers, and static contribute to the body rating of hair. For comparison, to the experts a body rating of 0 to 1 indicates no body, whereas a body rating of 1 to 2 indicates poor body, 2 to 3 indicates average body, 3 to 4 indicates good body and 4 to 5 indicates excellent body.

An improved body rating after two shampooings was observed in the hair swatch treated with a composition including 0.15% keratin hydrolyzate; however, more significant increases in body rating were observed when the keratin hydrolyzate content of the hair treating composition was increased to 0.25% by weight of the composition. At keratin hydrolyzate amounts of 0.25% and above by weight of the hair treating composition, not only is the curl retention property improved (FIG. 2), but the permanence of the hair body improvement also was significantly improved (FIG. 3). For example, if the hair treating composition includes 0.45% by weight of keratin hydrolyzate, the body rating is improved to almost 4 even two shampooings after hair treatment. It is expected that further increases in the amount of keratin hydrolyzate in the hair treating compositions could lead to further improvements in body rating. Furthermore, it is surprising and unexpected for the keratin-based protein hair treating composition of the present invention to provide such excellent body ratings when applied to natural undamaged hair because most proteins demonstrate improved body when applied to damaged hair since the protein can more easily penetrate the hair shaft.

In another series of experiments, thickened keratin hydrolyzate-containing compositions were applied to the hair. The thickened compositions were tested because thickened compositions generally are more easily applied to the hair. Therefore, the thickened hair-treating compositions of Example II were prepared by adding the ingredients in the order listed with thorough mixing to yield thickened compositions of pH 8.0 to 8.5.

Example II

| Thickened Hair Setting/Conditioning Compositions | | |
| --- | --- | --- |
| Ingredient | Wt % | Wt % |
| Soft Water | q.s. to 100% | q.s. to 100% |
| Hydroxyethyl cellulose (thickener) | — | 0.50% |
| Carbomer 940 (thickener) | 0.65% | — |
| Citric Acid or Sodium Hydroxide solution (pH adjustment) | q.s. to pH 8.0–8.5 | q.s. to pH 8.0–8.5 |
| Cystine-containing protein (KERASOL, available from Croda, Inc., N.Y., N.Y.; 15% by weight aqueous solution of keratin hydrolyzate, M.W. of approximately 125,000) | 0.06%–27% | 0.06%–27% |
| Preservative | q.s. | q.s. |
| Dye, fragrance and other optional ingredients | as desired | as desired |

Figure 4:
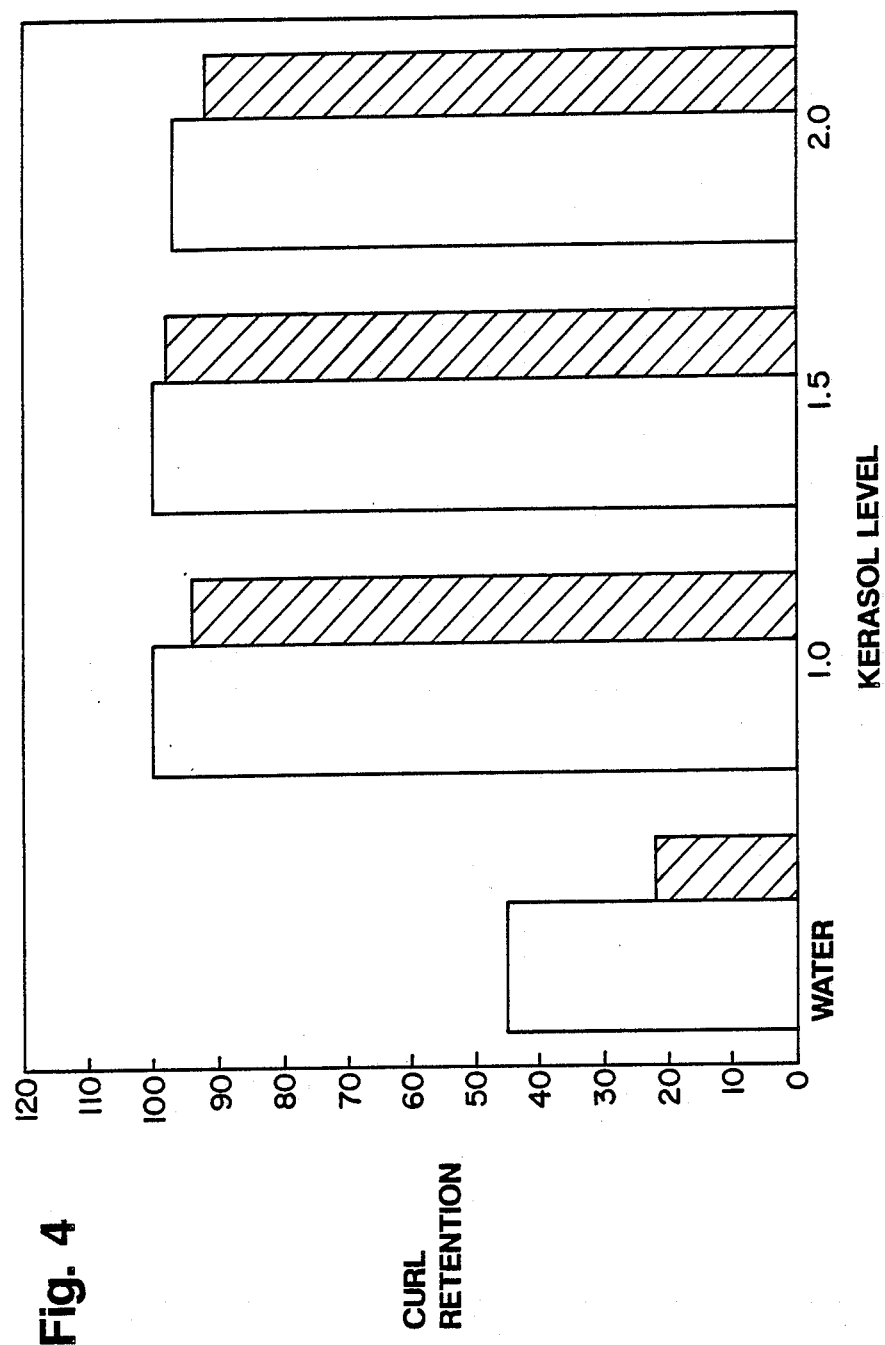
FIGS. 4 and 5 are graphs of % curl retention after one hour and after 24 hours vs. percentage amount of cystine-containing protein present in the composition used to treat the hair.
Figure 5:
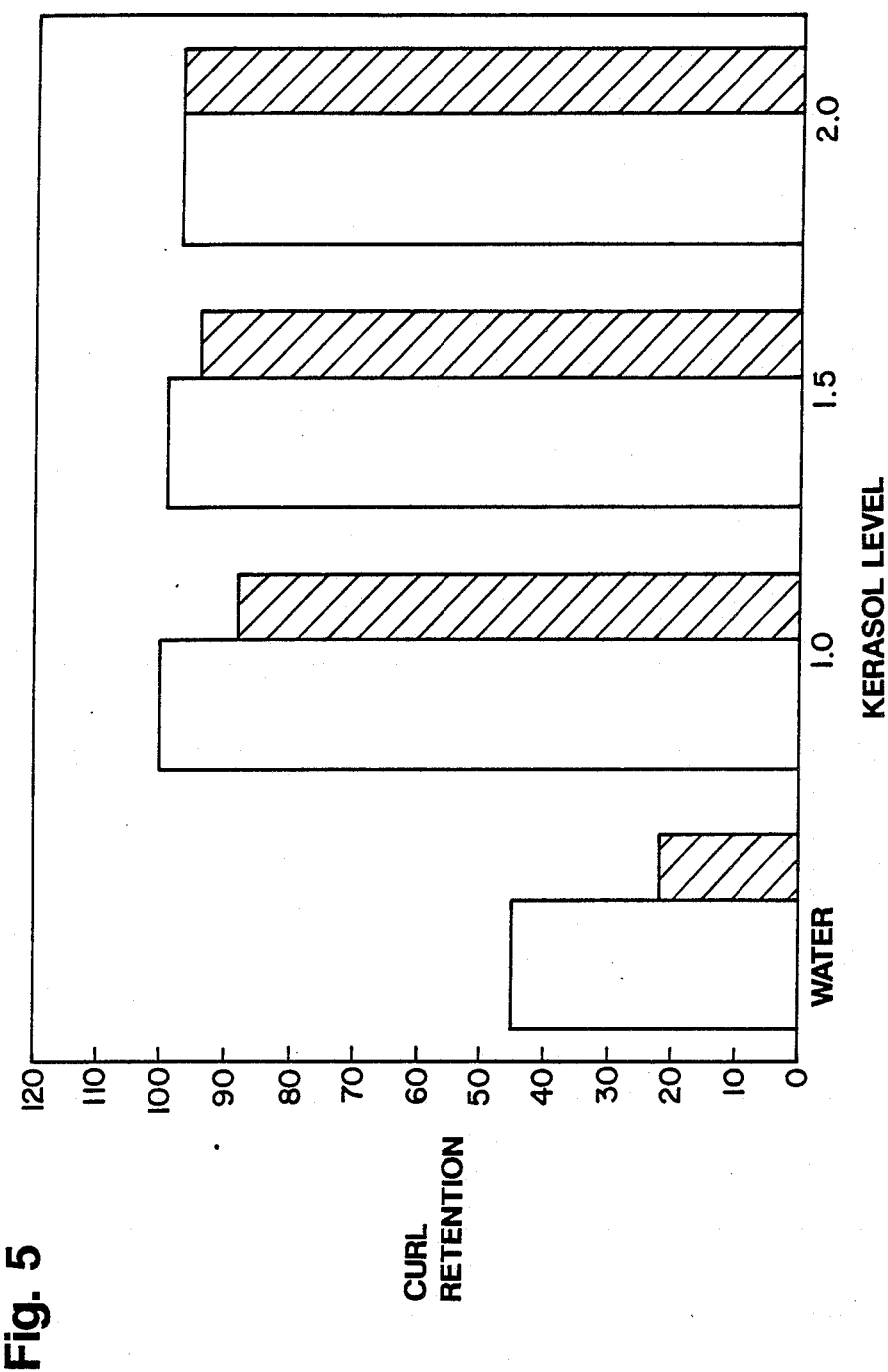

Various compositions of Example II were applied to hair tresses as previously described, and the curl retention tests were performed. The percent hair set retention results are summarized in FIGS. 4 and 5. It was observed that percent curl retention is improved substantially when a thickener is present in the composition of the present invention. FIG. 4 shows that hair treated with a hair setting composition including 0.65% by weight carbomer 940 and 0.15% keratin hydrolyzate demonstrates a curl retention of 100% after one hour and about 95% after 24 hours. FIG. 5 shows that hair treated with an almost identical composition including 0.15% keratin hydrolyzate, except that 0.50% by weight of the thickener hydroxyethyl cellulose replaced the carbomer 940, similarly demonstrated a 100% curl retention after 1 hour and an approximately 88% curl retention after 24 hours. In comparison, from FIG. 2, hair treated with an unthickened composition provided only a 65% curl retention after 1 hour and a 35% curl retention after 24 hours FIGS. 4 and 5 also demonstrate that hair treated with thickened compositions containing increased percentages of the keratin hydrolyzate also showed improved 24 hour percent curl retentions over hair treated with the unthickened compositions.

It has been theorized that some synergistic effect occurs between the thickener and the keratin hydrolyzate. However, it is more probable that the further improved curl retention properties of the thickened composition are a result of the rheology of the hair treating composition. The thickener acts to hold the hair setting composition on the hair tress for more intimate contact by preventing the hair setting composition from running down and off the hair, thereby facilitating the interaction between the hair and keratin hydrolyzate to occur.

Figure 6:
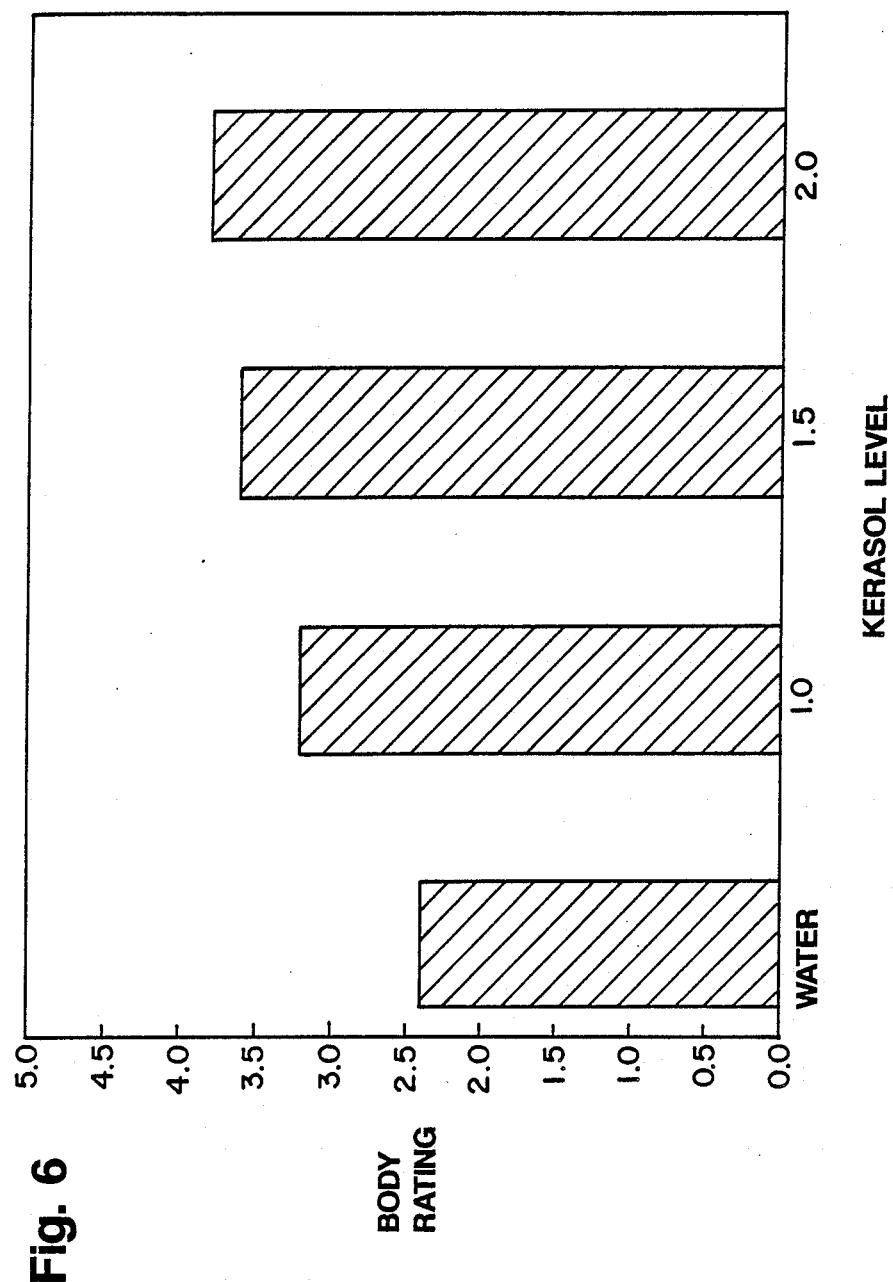
FIG. 6 is a graph of subjective body rating, showing the relative condition of the hair after two shampooings vs. percentage amount of cystine-containing protein present in the composition used to treat the hair.

The effect of two shampooings upon the body rating of hair treated with the thickened compositions of Example II is shown in FIG. 6. The identical hair shampooing procedure and the identical subjective evaluation was used as described above in relation to FIG. 3. A comparison of FIG. 3 to FIG. 6 shows that the subjective body rating of the treated hair is essentially the same for hair treated with either the thickened or the unthickened hair treating compositions of the present invention.

Figure 7:
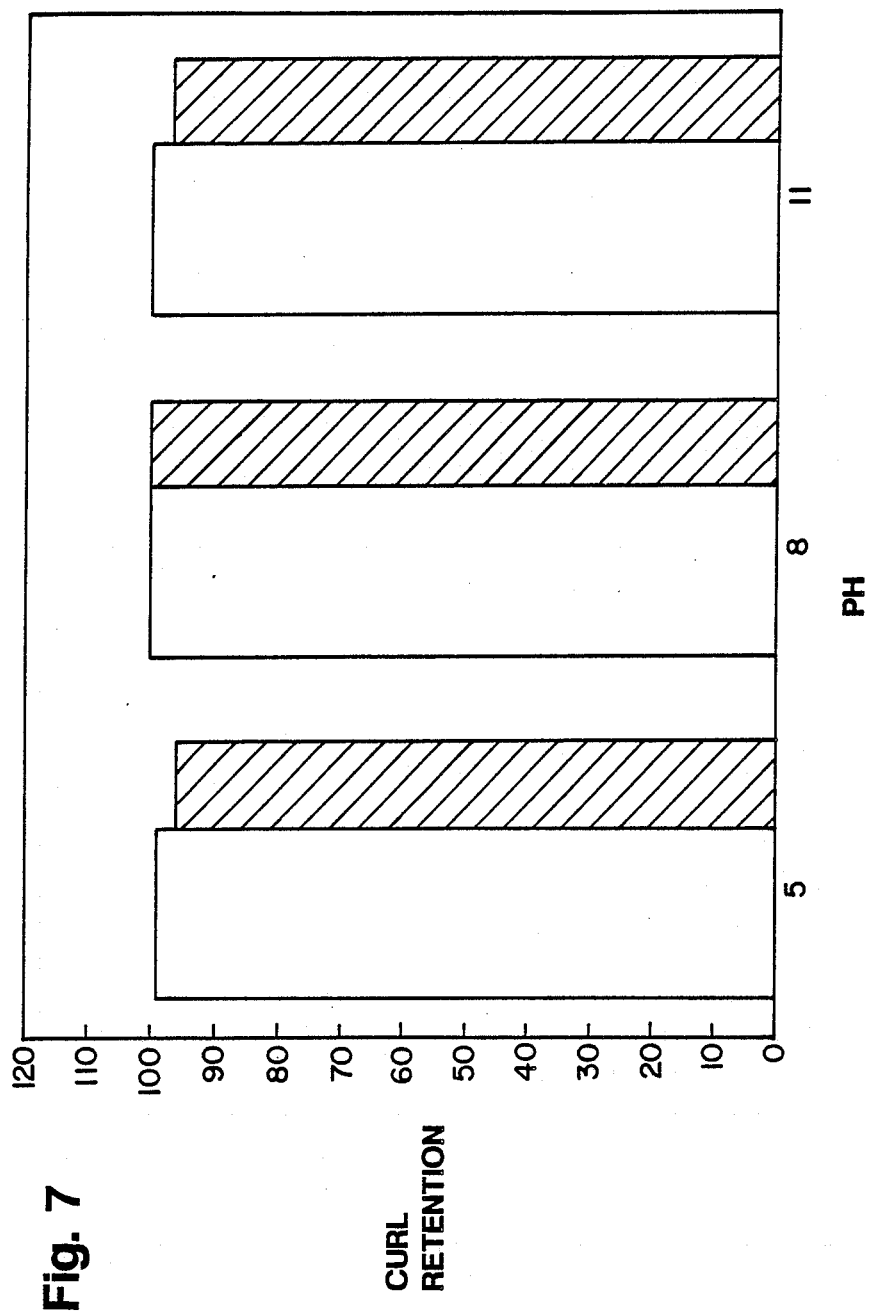
FIG. 7 is a graph of % curl retention after one hour and after 24 hours vs. pH of the cystine-containing protein composition used to treat the hair.
Figure 8:
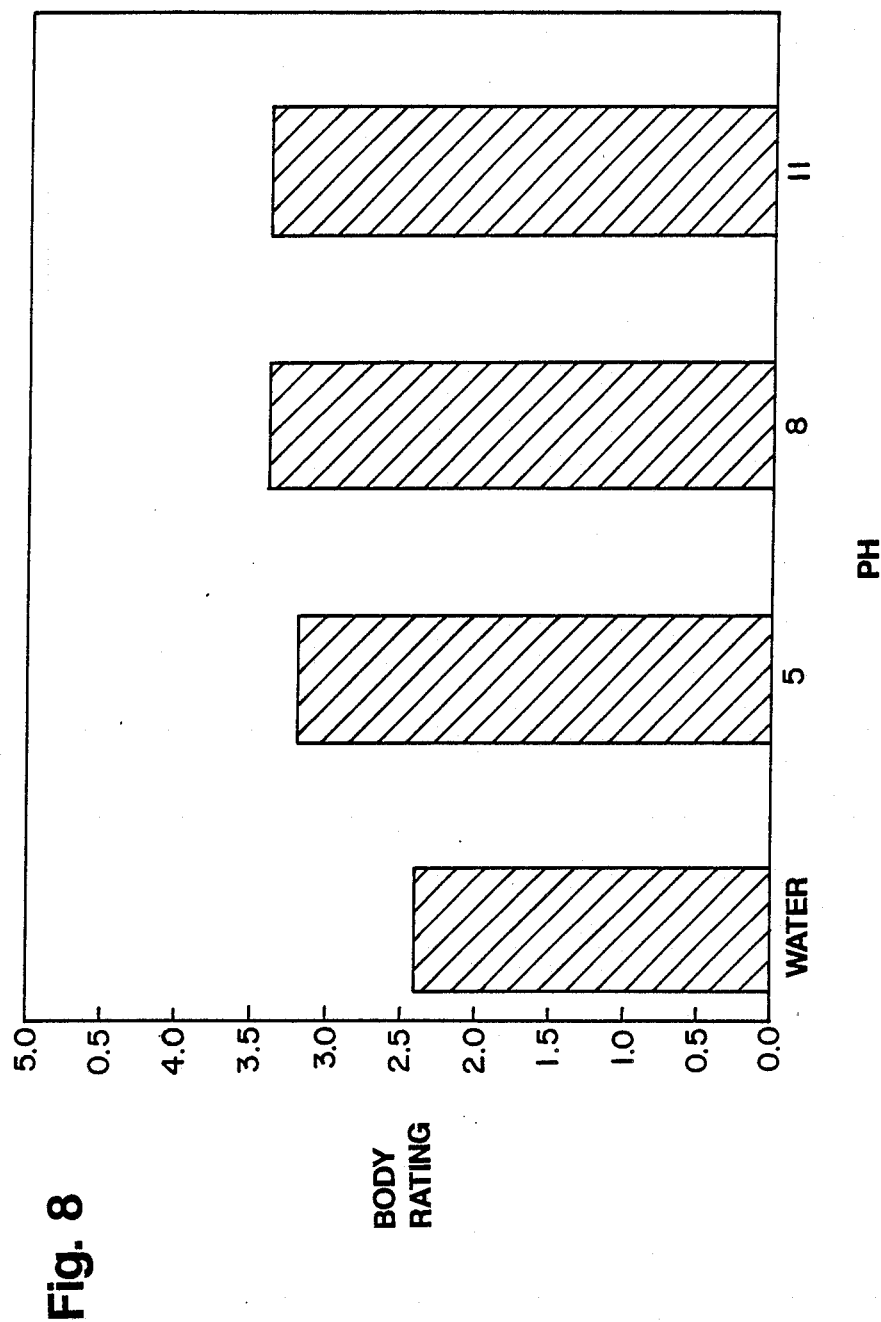
FIG. 8 is a graph of the subjective body rating showing the relative condition of the hair after two shampooings vs. pH of the cystine-containing protein composition used to treat the hair.

The effect of hair treating composition pH upon the curl retention properties of treated hair was demonstrated by adjusting the pH of the hydroxyethyl cellulose-thickened compositions of Example II, containing 0.15% of keratin hydrolyzate, to a pH of 10 to 12 and to a pH of 5 to 5.5. The hair treating compositions of differing pH were applied to the hair as described above, and the percent curl retention tests are summarized in FIG. 7. It is readily observed from the results graphed in FIG. 7 that the method and composition of the present invention is essentially pH independent as the percent curl retention, both after 1 hour and after 24 hours, is essentially identical over the pH range from about 3 to about 12. Similarly, FIG. 8 shows that the subjective body ratings after two shampooings also were essentially identical for hair treated with compositions of the present invention having a pH over the broad range of from about 3 to about 12.

Figure 9:
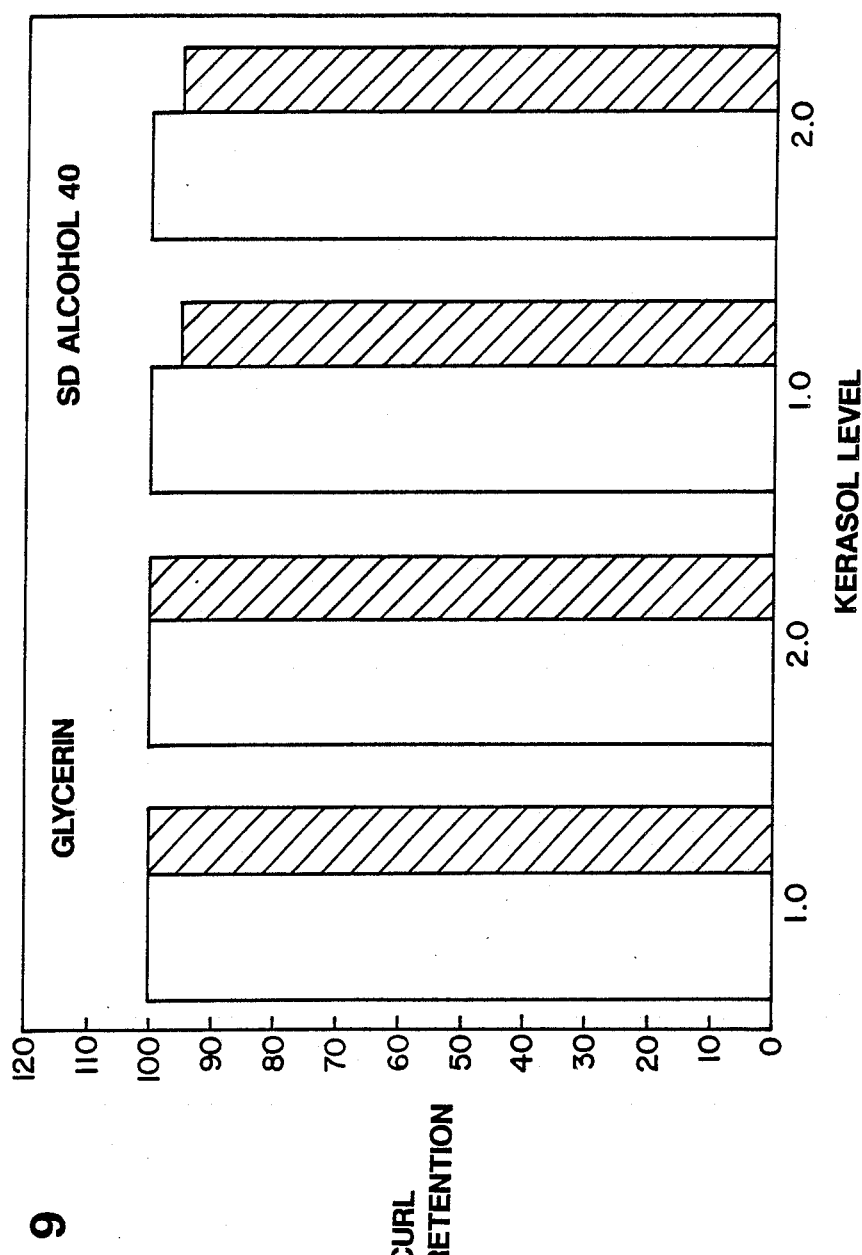
FIG. 9 is a graph of % curl retention after one hour and after 24 hours vs. percentage amount of cystine-containing protein present in compositions further including either glycerin or ethyl alcohol, and used to treat the hair.
Figure 10:
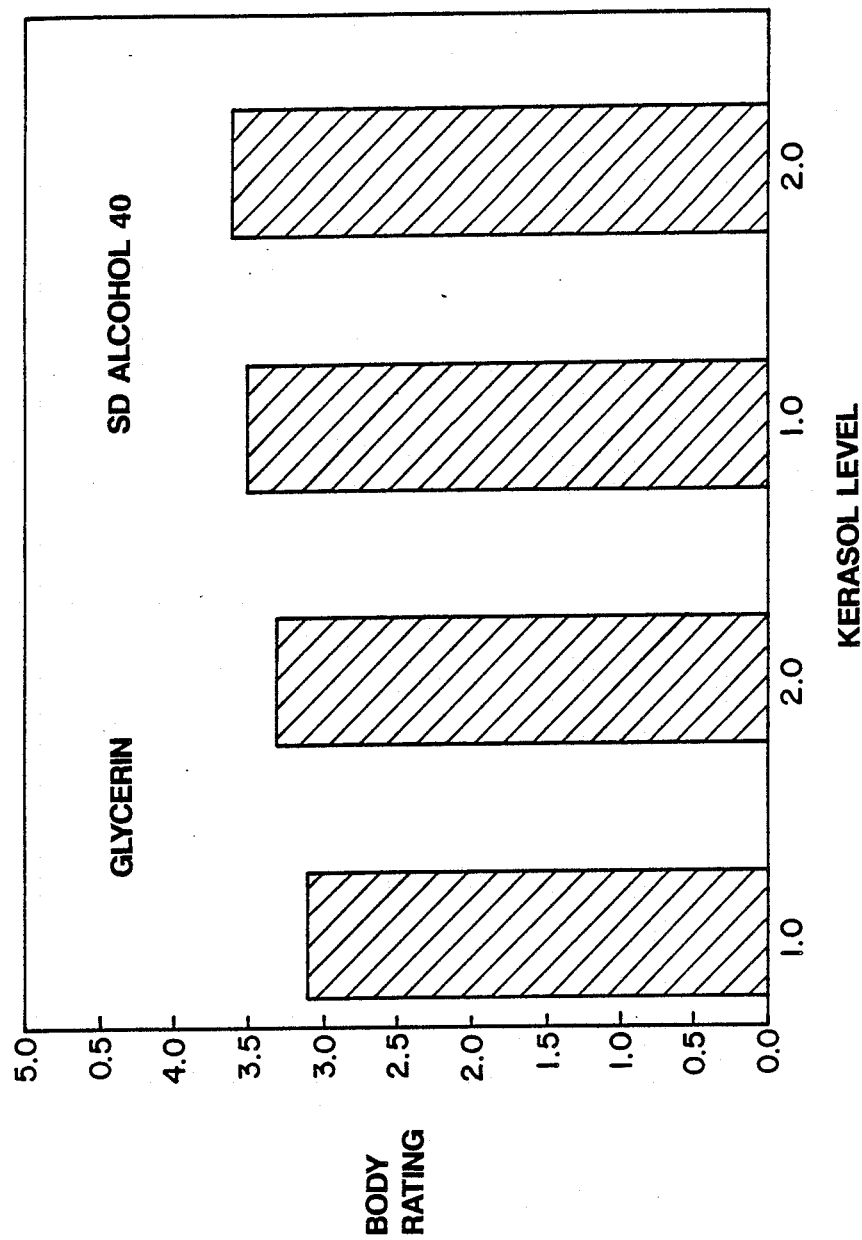
FIG. 10 is a graph of subjective body rating showing the relative condition of the hair after two shampooings vs. percentage of cystine-containing protein present in compositions further including either glycerin or ethyl alcohol, and used to treat the hair.

The effect of optional composition ingredients on the ability of the keratin hydrolyzate component of the composition to set the hair and to impart body to the hair also was tested. For example, FIGS. 9 and 10 show that the addition of a plasticizer/humectant, like glycerin, or a solvent/solubilizer, like ethyl alcohol, to a hair treating composition of the present invention including 0.15% of the keratin hydrolyzate did not adversely affect composition stability or consumer appeal. In addition, the hair treating compositions of the present invention that included either glycerin or ethyl alcohol provided the excellent percent curl retention to treated hair, both after 1 hour and after 24 hours (FIG. 9), and provided a good body rating to treated hair after two shampooings (FIG. 10), similarly observed in hair treated with compositions lacking the glycerin or ethyl alcohol.

Therefore, in accordance with the method of the present invention, after applying a hair-treating composition comprising a protein having a sufficient amount of an amino acid having a disulfide linkage, such as a keratin-based protein that includes the amino acid cystine, hair conditioning properties and hair set retention properties are improved sufficiently such that the hair setting composition does not have to be reapplied to the hair after each shampooing, and such that the desired hair set has the potential to last several days. Most notably, the benefits of a semi-permanent hair set are achieved in the method of the present invention without damaging the hair through harsh chemical reduction and oxidation steps. As shown in FIGS. 1 through 10, the disulfide-containing protein must include a sufficient amount of the disulfide-containing amino acid in order to provide a sufficient number of available disulfide linkages to react with the disulfide bonds in the hair. Similarly, the composition of the present invention must include a sufficient amount of the disulfide-containing protein to provide a sufficient amount of protein for reaction with the hair in order to condition the hair and impart semi-permanent curl retention properties.

In accordance with another important feature of the present invention, application of the present hair treating composition provides the benefits and advantages of improved hair conditioning and a semi-permanent hair set when the composition has a pH in the broad range of about 3 to about 12. In addition to exceptional durability, the hair setting compositions of the present invention, having a pH within the broad range of about 3 to about 12, also impart to the hair additional beneficial hair set properties demanded by the consumer, such as combability, gloss, softness and body.

A further benefit afforded by the method and composition of the present invention is that the time required for the hair to contact the hair treating composition in order to achieve the benefit of a semi-permanent hair set is relatively short. In contrast to the prior art hair setting compositions that require contact times of 15 minutes to 16 hours, the composition of the present invention effectively treats the hair within the time it takes to treat and dry the hair to yield a semi-permanent and esthetically pleasing hair set. It has been demonstrated that a composition of the present invention can effectively treat the hair as soon as the composition has dried on the hair, thereby appreciably shortening the time necessary to produce a semi-permanent hair set. In addition, it has been found that by allowing the composition of the present invention to dry on the hair at ambient temperature for relatively long times or to dry on the hair at elevated temperatures, such as by hot blow drying, for relatively short times, does not lead to any adverse effects on the hair either in regard to the semi-permanence of the hair set or to the esthetic properties of the hair set.

Although there are several commercial products in the marketplace to condition the hair and to improve the set holding properties of hair, such as setting lotions, gels and hair sprays, these products must be applied to the hair after each shampoo either prior to or during the styling process. However, in accordance with the method of the present invention, contacting the hair with a composition comprising a protein having a sufficient amount of an amino acid having a disulfide linkage, such as a keratin-based protein that includes the amino acid cystine, provides a hair set that is semi-permanent and resistant to at least three, and up to five to six, subsequent shampooings. As a result, a hair setting composition does not need to be reapplied to the hair before each hair styling, therefore making hair setting more convenient for the consumer.

In addition, the method of the present invention provides the further benefits of not leaving the hair tacky or sticky, unlike conventional setting lotions; not forming a crust and therefore providing combability, unlike conventional hair sprays; and not damaging the hair, unlike conventional permanent wave treatments. Further, the benefits afforded by the composition of the present invention are achieved regardless of whether the composition is applied in a rinse-off or a leave-on fashion. In addition, after treating the hair with the composition of the present invention, the set hair feels natural and thickened, has body, is soft, shiny, manageable, and combable, and retains the imparted hair style even under high humidity conditions. These beneficial effects can be achieved by using an aqueous or non-aqueous spray or solution formulation, emulsion formulation, shampoo formulation or a suitable combination of all three formulations. In general, the benefits and advantages of the present invention can be realized regardless of the end-use hair treating composition used to treat the hair, such as conditioners, hair sprays, shampoos, hair colors, bleaches or other fixatives.

Obviously, many modifications and variations of the invention as hereinbefore set forth can be made without departing from the spirit and scope thereof and therefore only such limitations should be imposed as are indicated by the appended claims.

I claim:

1. A method of imparting semipermanent hair set retention properties to hair comprising contacting the hair that is in a substantially chemically unreduced state with a hair treating composition, comprising an effective amount of a protein including an amino acid having a disulfide linkage, and a suitable liquid carrier, wherein the protein has a average molecular weight of at least 50,000 and wherein the composition has a pH of from about 3 to about 12; configurating the substantially unreduced hair into a desired hair set configuration; and subjecting the substantially unreduced treated hair to a drying step; rewetting the hair; and subjecting the substantially unreduced treated hair to a second drying step without an intermediate step of treating the hair with a hair setting composition prior to a second drying step while covalently bonding the protein to the substantially unreduced hair to retain an effective degree of the hair configuration.

2. The method of claim 1 wherein the protein includes at least 0.1% by weight of the amino acid having a disulfide linkage.

3. The method of claim 1 wherein the protein includes the amino acid cystine.

4. The method of claim 1 wherein the protein is a keratin-based protein.

5. The method of claim 4 wherein the keratin-based protein is a keratin hydrolyzate.

6. The method of claim 5 wherein the keratin hydrolyzate has an average molecular weight in the range of from at least 50,000 to about 1,000,000.

7. The method of claim 5 wherein the keratin hydrolyzate has an average molecular weight in the range of from at least 50,000 to about 300,000.

8. The method of claim 1 wherein the protein is present in an amount ranging from about 0.01% to about 20% by weight of the composition.

9. The method of claim 1 wherein the protein is present in an amount ranging from about 0.25% to about 3% by weight of the composition.

10. The method of claim 1 wherein the composition has a pH of from about 5 to about 11.

11. The method of claim 1 wherein the liquid carrier is selected from the group consisting of water, alcohols, glycols, glycol ethers and polyols; or combinations thereof.

12. The method of claim 1 wherein the liquid carrier is selected from the group consisting of water, ethyl alcohol, isopropyl alcohol, glycerol, 2-butoxyethanol, propylene glycol, ethylene glycol monoethyl ether, propylene glycol monoethyl ether, diethylene glycol monoethyl ether, propylene glycol monomethyl ether and diethylene glycol monomethyl ether; or combinations thereof.

13. The method of claim 1 wherein the liquid carrier comprises water, ethyl alcohol or isopropyl alcohol; or combinations thereof.

14. The method of claim 1 further comprising a thickener.

15. The method of claim 14 wherein the thickener is present in an amount of from about 0.1% to about 3% by weight of the composition.

16. The method of claim 14 wherein the thickener is present in an amount of from about 0.25% to about 1% by weight of the composition.

17. The method of claim 14 wherein the thickener is selected from the group consisting of sodium alginate, guar gum, xanthum gum, gum arabic, methylcellulose, hydroxyethylcellulose, hydroxypropylmethylcellulose, carboxymethylcellulose and polyacrylic acid; or combinations thereof.

18. The method of claim 1 further comprising from about 0.1% to about 20% by weight of a surfactant.

19. The method of claim 18 wherein the surfactant is an anionic surfactant, a cationic surfactant or a nonionic surfactant; or combinations thereof.

20. The method of claim 1 wherein the treated hair is rewet and dryed from one time to about four times without an intermediate treatment of the hair with a hair setting composition and after said rewetting and drying steps has retained the hair set configuration without having to retreat the hair with a hair setting composition.

21. A method of imparting durable hair conditioning properties to hair in a substantially unreduced state comprising contacting the substantially unreduced hair with a hair treating composition, comprising an effective amount of a protein including an amino acid having a disulfide linkage and an average molecular weight of at least 50,000, and a suitable liquid carrier, wherein the composition has a pH of from about 3 to about 12; configuring the treated substantially unreduced hair into a desired hair set configuration; and subjecting the treated substantially unreduced hair to a drying step; rewetting the hair; and subjecting the treated substantially unreduced hair to a second drying step without an intermediate step of treating the treated substantially unreduced hair with a hair setting composition prior to a second drying step while covalently bonding the protein to the substantially unreduced hair to retain an effective degree of the hair configuration.

22. A method of imparting semipermanent hair set retention properties to hair comprising contacting the hair with a hair treating composition, comprising an effective amount of a protein including an amino acid having a disulfide linkage and an average molecular weight of at least 50,000, and a suitable liquid carrier, wherein the composition has a pH of from about 3 to about 12; and wherein the hair has not been reduced immediately prior to contact with the hair treating composition.

23. The method of claim 22 wherein the protein includes at least 0.1% by weight of the amino acid having a disulfide linkage.

24. The method of claim 22 wherein the protein includes the amino acid cystine.

25. The method of claim 22 wherein the protein is a keratin-based protein.

26. The method of claim 25 wherein the keratin-based protein is a keratin hydrolyzate.

27. The method of claim 26 wherein the keratin hydrolzate has an average molecular weight in the range of from at least 50,000 to about 1,000,000.

28. The method of claim 26 wherein the keratin hydrolyzate has an average molecular weight in the range of from at least 50,000 to about 300,000.

29. The method of claim 22 wherein the protein is present in an amount ranging from about 0.01% to about 20% by weight of the composition.

30. The method of claim 22 wherein the protein is present in an amount ranging from about 0.25% to about 3% by weight of the composition.

31. The method of claim 22 wherein the liquid carrier is selected from the group consisting of water, alcohols, glycols, glycol ethers and polyols; or combinations thereof.

32. The method of claim 22 further comprising a thickener.

33. The method of claim 32 wherein the thickener is present in an amount of from about 0.1% to about 3% by weight of the composition.

34. The method of claim 28 wherein the thickener is present in an amount of from about 0.25% to about 1% by weight of the composition.

35. The method of claim 32 further comprising from about 0.1% to about 20% by weight of a surfactant.

36. The method of claim 35 wherein the surfactant is an anionic surfactant, a cationic surfactant or a nonionic surfactant; or combinations thereof.

37. The method of claim 22 wherein the treated hair is rewet and dryed from one time to about four times without an intermediate treatment of the hair with a hair setting composition and after said rewetting and drying steps has retained the hair set configuration without having to retreat the hair with a hair setting composition.

38. A method of imparting semipermanent hair set retention properties to hair in a substantially unreduced state comprising configuring the hair into a desired hair set configuration; contacting the substantially unreduced hair with a hair treating composition, comprising an effective amount of a protein including an amino acid having a disulfide linkage and an average molecular weight of at least 50,000, and a suitable liquid carrier, wherein the composition has a pH of from about 3 to about 12; and subjecting the treated substantially unreduced hair to a drying step while covalently bonding the protein to the substantially unreduced hair to retain an effective degree of the hair configuration.

* * * * *